US010195107B1

(12) United States Patent
Lee

(10) Patent No.: US 10,195,107 B1
(45) Date of Patent: Feb. 5, 2019

(54) SENSING CONTROL METHOD AND APPARATUS

(71) Applicant: American Latex Corp., Chatsworth, CA (US)

(72) Inventor: Calvin Spencer Lee, Northridge, CA (US)

(73) Assignee: American Latex Corp., Chatsworth, CA (US)

(*) Notice: Subject to any disclaimer, the term of this patent is extended or adjusted under 35 U.S.C. 154(b) by 0 days.

(21) Appl. No.: 15/887,845

(22) Filed: Feb. 2, 2018

(30) Foreign Application Priority Data

Dec. 29, 2017 (CN) .......................... 2017 1 1481936

(51) Int. Cl.
*A61F 5/00* (2006.01)
*A61H 19/00* (2006.01)
*A61H 1/00* (2006.01)

(52) U.S. Cl.
CPC ............... *A61H 19/44* (2013.01); *A61H 1/00* (2013.01); *A61H 2201/5007* (2013.01); *A61H 2201/5028* (2013.01); *A61H 2201/5064* (2013.01)

(58) Field of Classification Search
CPC .............. A61F 5/00; A61F 5/41; G05B 23/00
USPC ......................................... 600/38–41; 700/90
See application file for complete search history.

(56) References Cited

U.S. PATENT DOCUMENTS 8,734,321 B1 5/2014 Weller
9,437,096 B2 * 9/2016 Althaher ............ G08B 21/0446
2013/0060081 A1 3/2013 Carter et al.
2014/0142374 A1 5/2014 Makower et al.
2015/0196453 A1 7/2015 Wu

OTHER PUBLICATIONS

Amazon.com webpage printout of product sheet for Luoge Massager Charging Vibrator Multi-speed LCD Touch Screen Magic Wand; https://222.amazon.com/Massager-Charging-Vibrator-Multi-speed-Screen/dp/B00WLYPROC, Dec. 18, 2017, 4 pages.

Amazon.com webpage printout of product sheet for Sex Toy for Woman Baile Bi0141071 Pretty Love Fantasy Touch Screen Control 5 Speed 3 Motors G Spot Vibrator; https://www.amazon.com/Bi0141071-Fantasy-Control-Vibrator-Massager/dp/B00HDAHHA, Dec. 18, 2017, 3 pages.

* cited by examiner

*Primary Examiner* — Samuel Gilbert
(74) *Attorney, Agent, or Firm* — Danton K. Mak; Leech Tishman Fuscaldo & Lampl

(57) ABSTRACT

The invention provides a sensing control method and apparatus, and a vibration massage apparatus. The method comprises: arranging a sensor which senses a trajectory of an external object, and controlling the change of output based on the direction of the trajectory. With the invention, a desirable control effect can be obtained based on the sensed direction of the trajectory of the external object without accurate positioning of the sensor. Not only the convenience of the sensing operation can be improved significantly, but also the control accuracy can be improved; meanwhile, the invention can be well applied to any device for control using several input control signals or variable input control signals for control, thus having a wide range of application and significantly optimizing user experience.

18 Claims, 5 Drawing Sheets

*Fig. 1*
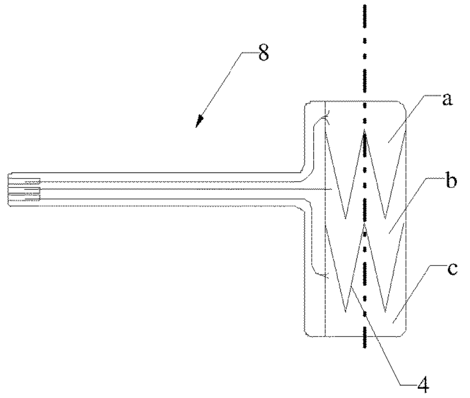
*Fig. 7*
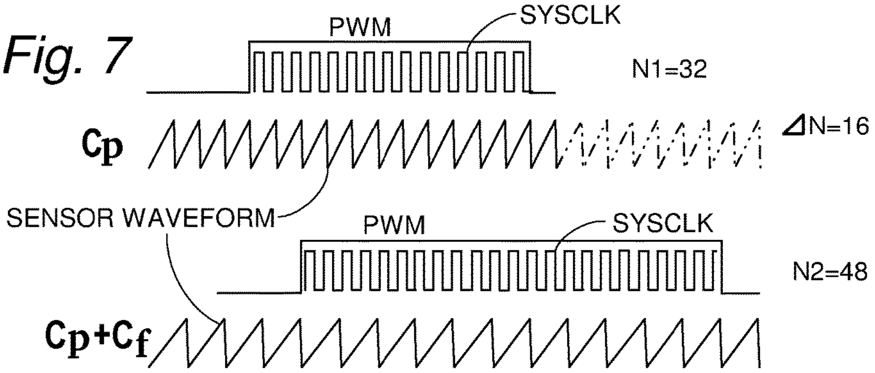
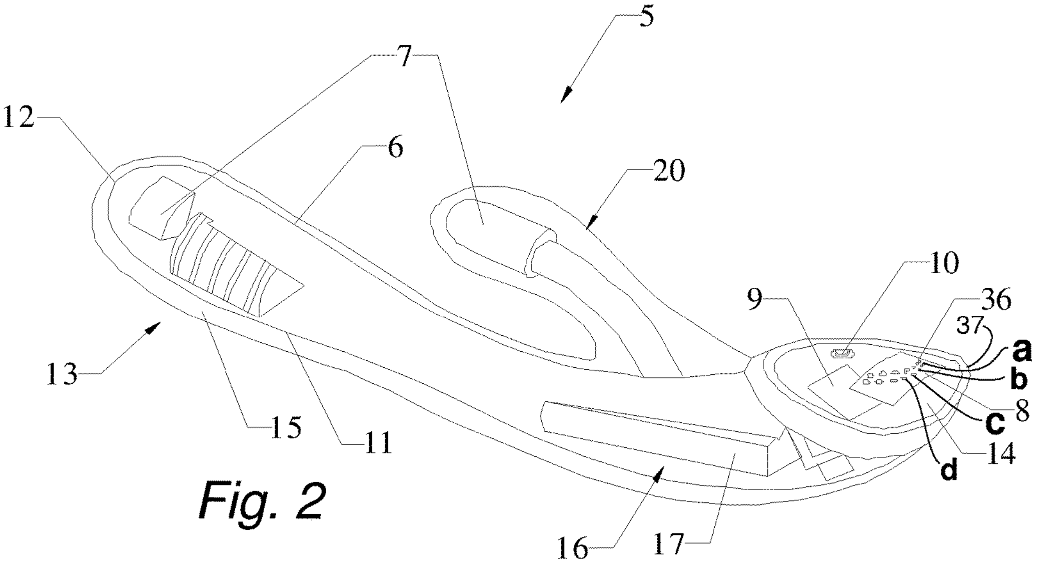
*Fig. 2*

SENSING CONTROL METHOD AND APPARATUS

CROSS-REFERENCE TO RELATED APPLICATIONS

This application claims priority from Chinese Patent Application No. 201711481936.0 titled "Sensing Control Method and Apparatus, and Massage Apparatus," filed Dec. 29, 2017, the contents of which are incorporated by reference herein in their entirety.

FIELD OF THE INVENTION

The invention relates to the field of drive control, and in particular to a sensing control method and apparatus, and a sexual stimulation massage apparatus.

BACKGROUND OF THE INVENTION

Existing sensing control methods of the prior art include sliding along a sensing control strip to control the change in an output (such as vibration intensity, heating intensity, rotation frequency, heat generation amount, etc.). This is by using a control strip configured as a capacitance sensing unit, through which the capacitance change in a corresponding region due to a sliding touch of a conductive substance (such as a finger) on the control strip is detected, and then an output is activated by triggering a control instruction corresponding to the region. Touch sensing is based on the principle of capacitive sensing and the technique of relaxation oscillator.

For example, a segmented massage system is disclosed in published United States Patent Application Publication No. 2013/0060081. As shown in FIG. 1 and FIG. 3 of the specification thereof, the segmented massage system is capable of selecting a desired mode through buttons 92, 94 and 96; then, when sliding conductive substance such as a finger on a triangular sensing copper sheet 90, different regions of the sensing copper sheet are touched. Since the touched regions of the sensing copper sheet have different areas, different capacitance values are detected by a capacitive sensing unit 50 located behind (see FIG. 1), thus realizing the output adjustment.

For the above-mentioned finger control mode of the prior art, the change in capacitance of the corresponding region due to the user's action is detected by the capacitance sensing unit, and the control is implemented by triggering the control instruction corresponding to the region. However, it is believed that the conductive media (such as the finger) used by different users for operating such a touch panel have individual differences (thickness/thinness, operational flexibility, proficiency, etc.); therefore, the operation may tend to deviate from the region which the user actually wants to touch. Thus, the corresponding instruction cannot be accurately triggered, and a desired control result cannot be obtained. If the contact area between the finger and the touch panel or the contact area that can be sensed by a proximity sensing unit is greater than or less than the area the user wants to touch in an ideal operation, mis-triggering or a non-ideal operation instruction will result, such that triggering of an intended operation instruction is unsuccessful.

Therefore, there is a need for a sensing control apparatus and method for improving control sensitivity, convenience, and reliability of appliances such as massagers, for more satisfactory user experience based on the sensing control.

SUMMARY OF THE INVENTION

The present invention meets this need by providing a sensing control method and apparatus, such as a sexual stimulation massage apparatus, for producing a desired control effect based on a sensed trajectory direction of an external object without needing to accurately position the external object relative to the sensor. Also, there is greatly reduced cost as compared with complex technologies, such as gaming, that use inertial tracking or similar devices. The sensing scheme of the present invention is different from other touch sensing technologies in that the sensitivity of each key can be adjusted independently. One chip can simultaneously implement the advantages of touching multiple touch keys and a touch scroll bar. This scheme can be used for a variety of home appliances instead of traditional touch buttons and membrane keyboard.

In one aspect of the invention, a sensing control apparatus includes a sensor and a main control unit (MCU) electrically connected to the sensor and having a control output, the sensor being configured for generating an electrical signal variation in response to a moving external object such as a user's finger; and the main control unit is configured for acquiring a trajectory direction of the external object in response to the electrical signal variation of the sensor and changing the control output based on the trajectory direction, wherein the external object can be spaced away from the sensor. Importantly, the sensed trajectory direction does not depend on whether the external object is in contact with the sensor, spaced from the sensor, or even intermittently in contact with the sensor. The term "moving external object" is no part of the claimed apparatus and normally is not acted upon by the apparatus, notwithstanding the possibility that other parts of a user's anatomy may be acted upon than that (such as the user's finger) which is to be sensed by the sensor.

Preferably, the sensor has at least two sensing units for generating corresponding sensor unit outputs, and the trajectory direction of the external object is acquired by the main control unit according to a relative distribution of the sensor unit output variations. The main control unit can be configured for determining whether to acquire the trajectory direction according to whether the sensor unit output variations exceed a preset value.

Preferably the trajectory direction is acquired by the main control unit based on at least two of the sensing units being aligned with an expected trajectory path.

Preferably adjacent sensing units in the sensor are separated by a gap. Preferably at least a portion of the gap is oriented obliquely relative to the expected trajectory path. More preferably the gap forms a zigzag pattern for consistent sensor operation more tolerant of lateral trajectory variations.

Preferably there are at least three sensing units, there being correspondingly at least two of the gaps between adjacent pairs of the sensing units.

Preferably, if the same direction of the trajectory is sensed continuously, the main control unit controls the control output correspondingly continuously increasing or decreasing. Preferably if opposite directions of the trajectory are sensed continuously, the main control unit controls the control output to be changed in an opposite direction to a previous change of output.

Preferably the main control unit is further configured for storing a current output level and a current output control mode in response to a turn-off operation of the user.

Preferably at least one output control mode is stored in the main control unit, and the main control unit is further configured for analyzing an acquired operation instruction and for activating the at least one output control mode in response to a user operation.

Preferably the control output is in the form of a pulse-width-modulated (PWM) signal. Preferably the PWM signal is controlled by the main control unit based on the trajectory direction of the external object.

As outlined above, the sensing control apparatus of the present invention provides an accurate control output based on user's gestures that do not have to be precise, and without regard to whether the external object is spaced away from or contacts the sensor. This is advantageous in terms of convenience and usability as compared with a control mode of the prior art in which the external object is required to be positioned accurately.

In another aspect of the present invention, a vibration massage apparatus includes a housing; a vibrator arranged inside the housing; a sensor arranged close to the housing; and a main control unit connected to the sensor and having a control output connected to the vibrator, characterized in that the main control unit is configured for acquiring a trajectory direction of a spaced external object sensed by the sensor and for changing the control output to the vibrator, based on the acquired trajectory direction. A vibration speed of the vibrator can be increased or decreased by the main control unit based on the acquired trajectory direction.

Preferably the sensor has at least two sensing units for generating corresponding electrical signal variations; and the trajectory direction is acquired by the main control unit according to the relative distribution of respective sensor unit output variations. Preferably the trajectory direction is acquired by the main control unit based on at least two of the sensing units being aligned with an expected trajectory path. Preferably, adjacent sensing units in the sensor are separated by a gap.

Preferably at least a portion of the gap is oriented obliquely relative to the expected trajectory path for smoothing sensor operation. More preferably the gap forms a zigzag pattern for consistent sensor operation more tolerant of lateral trajectory variations.

Preferably there are at least three sensing units, and the sensing units are distributed adjacently and separated by respective gaps.

The trajectory direction can be acquired during a preset time interval. Preferably, if the same direction of the trajectory is acquired continuously, the control output which drives the vibrator is correspondingly continuously increased or decreased. Conversely, if opposite directions of the trajectory are sensed continuously, the main control unit controls the control output to be changed in an opposite direction to a previous change of output.

Preferably, a control key is located on the housing, the control key being connected to the main control unit; at least one output control mode is stored in the main control unit; and the main control unit is configured for selectively activating or turning off the vibrator, and setting an output control mode corresponding to the operation, in response to a user's control key operation. The vibration massage apparatus can further include a storage unit, the storage unit being connected to the main control unit, and configured for storing the output control mode and the control output by which the main control unit currently drives the vibrator when the main control unit responds to a user's operation of turning off the vibrator.

In one variation of the present invention, the housing has a main outer surface of a substantially cylindrical shape, an insertable portion of the housing being formed by a rounding at a first end portion of the main outer surface, and the sensor is located away from the insertable portion. Preferably an opposite second end portion of the main outer surface forms an approximate plane, the sensor being located close to the approximate plane.

Preferably the vibration massage apparatus further includes a battery assembly located inside the housing, the battery assembly having a battery pack and a charging circuit connected to the battery pack, the battery assembly being connected for powering the vibrator and the main control unit, and the charging circuit being adapted for receiving power from an external power source. A charging socket located proximate the second end portion of the main outer surface can be connected to the charging circuit for receiving external power, and a sealing cap for the charging socket can be tethered at a position on the sleeve near the charging socket. Preferably a sleeve covers at least the insertable portion of the main outer surface.

The vibration massage apparatus of present invention thus provides numerous advantages in that the direction of the trajectory of the external object is obtained through sensing, and the output is accurately controlled based on the direction of the trajectory. It is thus easier for the user to perform an operation to form the condition of triggering the control, and it is easier for the apparatus to identify and acquire the sensing result so that the user can conveniently obtain a desired control effect through a simple operation In another variation of the present invention, a vibration dildo includes the above outlined vibration massage apparatus, and the main outer surface is of a shape of an erect penis. Preferably the sensor can be touched during massage. Preferably a sleeve covers at least the insertable portion of the main outer surface.

Preferably the sleeve further includes a laterally protruding arm, an auxiliary vibrator being located in the arm and connected to the main control unit. Preferably the sensor is located away from the insertable end portion and the arm.

Preferably an end surface of the housing opposite the insertable end portion has an approximately planar region that is angled obliquely upward and close to the arm, and the sensor is located close to the approximately planar region.

Preferably the sensor has at least three adjacent sensing units that are arranged in an arc shape or in a straight line, preferably separated by zigzag gaps. Optionally, the sensor units are of a Z shape.

The above-described technical solution of the invention has the following advantageous effects. In the vibration dildo as provided, the vibration speed is accurately controlled based on the sensed direction of the trajectory. It is easier for the user to perform an operation during massage to form the condition of triggering the control of the vibration speed; it is also easier for the device to identify and acquire the sensing result, and it is convenient for the user to obtain the actual desirable control effect through a simple operation.

In a further aspect of the present invention, a sensing control method includes providing a sensor for sensing an external object, and providing a control output responsive to sensor signals, characterized in that the control output changes in response to a sensed trajectory direction of the external object which can be spaced away from the sensor.

Preferably the control output changes are for increasing or decreasing a control intensity.

Preferably the sensor has at least two sensing units, and the trajectory direction of the external object is acquired according to a relative distribution of the sensor signals. The trajectory direction can be sensed during a preset time interval.

Preferably at least two adjacent sensing units are aligned with an expected trajectory path.

Preferably, if the same direction of the trajectory is sensed continuously, the control output is correspondingly continuously increased or decreased. Conversely, if opposite directions of the trajectory are sensed continuously, the control output is changed in an opposite direction to a previous change of output.

Preferably the method further includes the steps of presetting at least one output control mode, and activating the output control mode in response to a user operation. Preferably the method further includes storing a current output level and a current output control mode in response to a turn-off operation of the user. Thus the method can be conveniently resumed at a previous output level and control mode.

In the sensing control method provided by the present invention, the direction of the trajectory of an external object is obtained through sensing, and the output is accurately controlled based on the direction of the trajectory. As compared with a control mode of the prior art in which the sensing position is required to be positioned accurately to trigger a corresponding action the control effect is often unsatisfactory, especially under dim or dark lighting.

BRIEF DESCRIPTION OF THE ACCOMPANYING DRAWINGS

These and other features, aspects, and advantages of the present invention will become better understood with reference to the following description, appended claims, and accompanying drawings, where:

FIG. 1 is a schematic structure diagram of a sensor according to the invention;

FIG. 2 is a schematic diagram showing structural components of a vibration massage apparatus incorporating the sensor of FIG. 1;

FIG. 7 is a waveform diagram showing operation of the OWM detector of FIG. 6;

Figure 3:
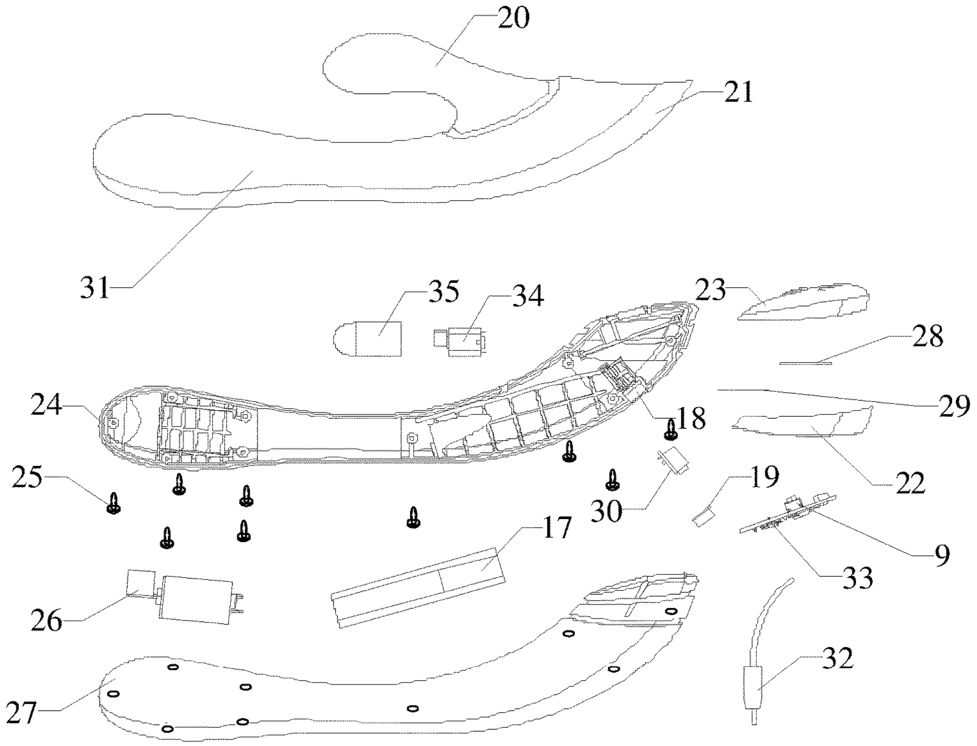
FIG. 3 is an exploded structure diagram of the massage apparatus of FIG. 2.
Figure 6:
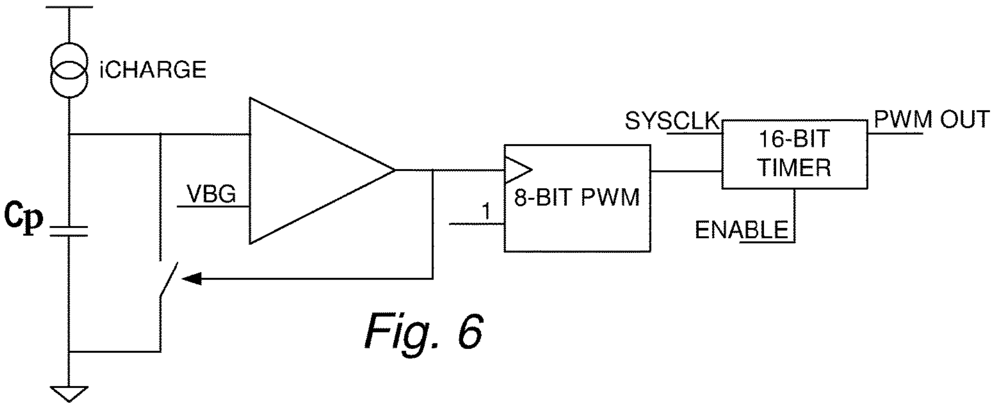
FIG. 6 is a simplified circuit diagram showing a PWM detector for a sensor unit of the present invention.

List of Reference Signs:

a-c. sensing units; P. expected path; 4. Zigzag gaps; 5. Vibration massage apparatus; 6. housing; 7. vibrator; 8. sensor; 9. main control unit; 10. control key; 11. main outer surface; 12. rounding; 13. insertable portion; 14. approximate plane; 15. sleeve; 16. battery assembly; 17. battery pack; 18. charging socket position; 19. sealing cap; 20. arm; 21. silica gel leather case; 22. electroplated ring; 23. silica gel back cover; 24. lower cover of housing; 25. screw; 26. motor of main body; 27. upper cover of housing; 28. flexible board EVA; 29. flexible board; 30. charging PCB board; 31. main portion; 32. charging wire; 33. PCB board; 34. motor of arm; 35. motor cover; 36. bumps or pits; 37. second end; 38. main output; 39. auxiliary output; 100. control method.

DETAILED DESCRIPTION OF THE PREFERRED EMBODIMENTS

The present invention is directed to drive control method and apparatus responsive to gestures of a user, as in controlling massaging devices and other electrical appliances. With reference to FIG. 1 of the drawings, a key component of the present invention is a sensor 8 having plural sensor units, three such being shown and designated a, b, and c, respectively, there being a gap 4 between each adjacent pair of sensor units as further described below. Together the sensor units occupy a region of length L along an expected trajectory path P of an external object, and a width W transverse to the expected trajectory path.

The main concept of the invention is to acquire the direction of a trajectory of the external object such as a user's finger through proximity sensing and to accurately control an output based on the direction of the trajectory. This invention is especially effective in controlling such variables as vibration intensity, heating intensity, rotation frequency, heat generation amount, etc. through the sensing of the user's gestures that need not be precise. Thus the present invention is advantageously applicable to controlling fans, heaters, ovens, air conditioners, etc.

The sensor can generate different electrical signal variations (which may be pulse variations, electrical signal variations such as current or voltage variations) based on different distances between a sensing point on a sensing detection circuit of the sensor and the external object when the external object approaches the sensor, and the trajectory of the external object and the direction of the trajectory are acquired by analyzing sensor signal variations. Preferably, when the electrical signal variation at a sensor unit caused by the external object reaches a preset threshold value, then that sensor unit activation is recorded, and a trajectory point is determined and recorded. Employment of the preset threshold value insures that the sensing result is more accurate, and mis-triggering of the trajectory point is avoided. A subsequent sensor unit activation defines a direction of the trajectory relative to an expected trajectory path along on which the sensor units are located.

After the direction of the trajectory of the external object is obtained, a change of a control output is effected according to different control instructions corresponding to different preset directions of the trajectory. For example, the direction of the trajectory from left to right can be preset to cause the intensity of the output for that trajectory direction of the external object to be increased correspondingly; if the trajectory direction is from right to left, then the intensity of the output would be decreased correspondingly.

It will be understood that in the case of a single sensor unit, the trajectory direction would be toward the sensor unit upon the signal variation reaching the preset value, then away from the sensor unit when the signal variation falls below the preset value. In the embodiments further described herein, the sensor has at least two sensing units, and the trajectory of the external object can be acquired according to the distribution of the sensing units. Since the distribution positions of the sensing units are fixed, if the variation value of the electrical signal of the sensing unit caused by the external object reaches a preset value, then it is determined that the corresponding sensing unit is activated, and a relative distribution of the variation of the electrical signal is generated. Therefore, the direction of the trajectory can be determined according to the sequential order of sensing the external object. For example, the sensing units designated a and b can be in order from left to right; if the approaching of the external object is sensed by a and b sequentially, it can be determined that the sensed trajectory direction is from left to right. It should be noted that, if the external object is sensed by the sensing unit designated a and the sensing unit designated b simultaneously, since there is no trend of direction change, the direction of the trajectory cannot be formed, and the control of the output will not be triggered.

Preferably, the sensor has at least three sensing units a, b, and c as shown in FIG. 1, more preferably, there are more than three. Small actions of the external object can be accurately sensed through partitioned sensing, and it is advantageous for determining the direction of the trajectory more efficiently and accurately. For example, a short sensing trajectory is formed on the sensor when a user approaches the sensor. If the number of the sensing units constituting the sensor is appropriate and the gap between the sensing units is appropriate, a short trajectory can be sensed by at least two sensing units, and the direction of the trajectory can be determined efficiently according to the distribution of sensing units.

Preferably, at least two adjacent sensing units are arranged along an expected trajectory path P to form the trajectory direction. That is, only if the single operation of the user is sensed sequentially by at least two adjacent sensing units in the sensor, the control of the output can be triggered. Accordingly, the sensor is preferably provided with at least two adjacent sensing units. Preferably, if the external object is sequentially sensed by two sensing units that are not adjacent to each other, the condition of triggering control is not met. For example, with the sensing units designated a, b and c from left to right, and only a-b, b-c, a-b-c, c-b, b-a, c-b-a can form the direction of the trajectory, wherein a-b means that the approaching of the external object is sensed by the sensing unit designated a and the sensing unit designated b sequentially. If the external object is sensed by the sensing unit designated a and the sensing unit designated c sequentially, but is not sensed by the sensing unit designated b, the direction of the trajectory is not be formed. What this accounts for is the possibility that unit a is first approached left to right; then the external object moves around (farther from) unit b, and then approaches unit c from the right. It would be erroneous to define a left to right trajectory direction.

Further, the trajectory sensed by the sensor is preferably valid only if it is sensed during a preset time. Moreover, the trajectory direction should be sensed by two adjacent sensing units within the preset time interval. Therefore, even if a trajectory is formed by triggering successive sensing units in sequence and the direction of the trajectory can be obtained, if the total length of time for acquiring the trajectory exceeds the preset time, the sensing result should be considered to be triggered after the preset time has been exceeded, the trajectory should not be based on activation of an initially activated sensor unit. For example, when the sensing units are designated a, b and c from left to right; if the external object is sensed by the sensing unit designated a, even if the external object is sensed by the sensing unit designated b after the preset time has been exceeded, the direction of the trajectory should not be defined. Accordingly, as to the operation of the user, if the user approaches the sensing unit designated b, pauses for a few seconds (assuming that the preset time has been exceeded), and then approaches the sensing unit designated c again, such operation should be considered to be invalid and the direction of the trajectory of b-c should not be sensed. Thus it is preferred that only if the direction of the trajectory is sensed through consistent operations will the control of the output be triggered, avoiding occurrence of mis-triggering and improving the accuracy of the operation. A possible variation is that after hovering over the sensor unit designated a beyond the time limit, the external object might pass quickly over units b and c, thus establishing a valid trajectory direction.

Preferably, the control instruction corresponding to the direction of the trajectory is triggered only after the external object is no longer sensed by the sensor. That is, only if the external object (such as a finger) used by the user for operation leaves the sensing range of the sensor, the detection result of sensing the direction of the trajectory is regarded as a valid input.

In the present exemplary embodiments, a single sensing event forms only one corresponding trajectory direction, and accordingly, the output is caused to change by a preset amount, such as increasing by 5%. If the same trajectory direction is sensed subsequently, the output is preferably controlled to be increased again by a preset amount continuously and incrementally according to the number of times of sensing the direction of the trajectory. For example, if a trajectory in a direction from left to right is sensed firstly, the output is controlled to be increased by 5%. On this basis, if the trajectory in the direction from left to right is sensed again, the output is controlled to be increased by another 5% over the previous output. If the user performs operations in the same direction repetitively, the control effect of increasing or decreasing the output incrementally is achieved. The increments can be arithmetic (fixed), or geometric (proportionally increasing or decreasing).

If opposite directions of the trajectory are sensed continuously, the output is changed in an opposite direction to the previous output change. That is, if completely opposite directions of the trajectory are sensed successively, the output is controlled to be increased firstly and then decreased, or be decreased firstly and then increased. For example, if the trajectory in the direction from left to right is sensed firstly, then the output is controlled to be increased by 5%. On this basis, if the direction of the trajectory is sensed next time to be from right to left, the output is controlled to be decreased by 5% back to what it was before the 5% increase.

With further reference to FIGS. 2-10, a sensing control apparatus in the form of a vibration massage apparatus 5 is provided according to the present embodiment, which includes: the sensor 8, and a main control unit 9 electrically connected to the sensor. The sensor 8 is configured for generating an electrical signal variation in cooperation with the main control unit 9 upon the approaching of an external object; and the main control unit is configured for acquiring a trajectory direction of the external object according to electrical signal variations of the sensor and for controlling a change of output (a main output 38 and an auxiliary output 39 being shown in FIG. 4) based on the direction of the trajectory. When an electrical signal variation is generated at a sensing point of the sensing detection circuit for the sensor due to the approaching of the external object, it is determined by the main control unit whether the corresponding sensing point is activated according to whether the electrical signal variation has reached a preset trigger value or not. Optionally, the trajectory may be determined according to the distribution of the activated sensing points, and the direction of the trajectory may be determined according to an order of the sensing units being activated.

Preferably, the sensor has at least two sensing units; more preferably, the sensor has at least three sensing units. Herein, the sensor is composed of several sensing units that interact with the main control unit to acquire the trajectory of the external object and the direction of the trajectory as described above. Further details are presented below regarding the sensing control method of the present invention.

Preferably, the sensor according to the embodiment is a proximity sensor. The sensing is triggered as long as the approaching of the external object is sensed, and there is no need to touch the surface of the apparatus. The above-mentioned proximity sensor may include a relaxation oscillator.

It should be emphasized that the adjacent sensing units in the sensor according to the present embodiment preferably are separated by gaps in the form of zigzags, W shapes or Z shapes, it being preferred that at least a portion of each gap be oriented obliquely relative to the expected trajectory path P. For example, the number of the sensing units can be three, the three sensing units being arranged as three points, three rings, three parallel lines or other shapes, each of which can realize the sensing control of the present invention. The separating gaps between the adjacent sensing units are formed as zigzags so that the adjacent sensing units in the sensor along paths parallel to the expected path P are staggered with each other, thus the external object such as a finger can be easily sensed by the two adjacent sensing units successively in shorter travel distances, and the trend of direction is detected to acquire a valid direction of the trajectory. This form of zigzag separation makes it easier for the adjacent sensing units to sense the direction of the trajectory, which is more convenient for user operation and is also advantageous for improving the sensing sensitivity.

Further, the width W of the path of the sensor is preferably greater than the width of a typical external object such as a finger, being between 15 and 100 mm, more preferably approximately 30 mm Preferably, the sensor is designed in a sheet shape, at least three sensing units being staggered with each other in a zigzag manner to form a sensing region of the sensor that has a length L in the direction of the expected path P. The length L of the sensor corresponds to a distance by which the external object can move, being long enough for reliable trajectory direction detection. The above-mentioned length L may be in a range from 15 mm to 100 mm, preferably it may be about 30 mm.

As further described below in connection with the sensing control method, the above-described control apparatus may be applied to any electrical device using several input control signals or variable input control signals, and for a control apparatus having a high temperature, the control apparatus may have a heat-insulation backing, thus insulating the sensing region from heat, and protecting the finger or other body part of the user from being scalded.

In another exemplary configuration of the present invention, a vibration massage apparatus is very effective in stimulating body parts, such as female genitals.

With particular reference to FIG. 2, the vibration massage apparatus 5 includes an elongated housing 6, at least one electric vibrator 7 arranged inside the housing 6, a main control unit 9, and a counterpart of the sensor 8 arranged close to the housing 6. The main control unit 9 is connected to the at least one vibrator 7 and the sensor 8 respectively. The housing 6 has a main outer surface 11 of a substantially cylindrical shape, an insertable portion 13 being formed by a rounding 12 at an end of the main outer surface 11, and the sensor 8 is located at a position away from the insertable portion 13, to be accessible during the massage of the user. Hereinafter, an example in which the external object is a finger of the user and the massage apparatus senses the external object to control the vibration speed is described in further detail herein.

The sensor 8 in the massage apparatus can generate different electrical signal variations according to different distances from the sensing point on the sensor 8 to the finger when the finger approaches the sensor, and sends the electrical signal variations to the main control unit. The main control unit analyzes the electrical signal variations upon receipt thereof, acquires a trajectory direction corresponding to a finger action sensed by the sensor and the direction of the trajectory, and controls the change of the vibration speed of the vibrator based on the direction of the trajectory. For example, if the direction of the trajectory from right to left is acquired, the vibration speed is controlled to be increased; and if the direction of the trajectory from left to right is acquired, the vibration speed is controlled to be decreased. In this embodiment, the approaching of the finger sensed by the sensor may also mean that the electrical signal variation of the sensing point on the sensor caused by the finger reaches a preset value.

Preferably, the sensor 8 has at least two sensing units, there being three of the sensing units, designated a, b, and c, respectively, as described above in connection with FIG. 1. The main control unit 9 can acquire the direction of the trajectory according to the distribution of the sensing units. Specifically, the direction of the trajectory is determined based on a sequence of the approaching of the finger as sensed by the sensing units according to physical locations of the sensing units. Preferably, the sensor has more than three sensing units, sensing units a, b, and c, etc., there being four, a, b, c, and d indicated in FIG. 2. The main control unit 9 can realize an accurate sensing of a tiny action (for example, sliding by a short distance) of the finger through partition sensing, and acquire the corresponding direction of the trajectory. As long as the number of the sensing units constituting the sensor is appropriate and the gap between the sensing units is appropriate, a short trajectory of the finger can be sensed by at least two sensing units, and the direction of the trajectory can be determined efficiently according to the locations of the sensing units. The sensing units in the sensor 8 are distributed adjacent to each other but are not connected end to end; and they may be arranged in a curved or arc shape, or in a straight line as shown in FIG. 1. They may also be in a band-like encircling arrangement. It is thus convenient for user operation and also convenient for the main control unit to determine the direction of the trajectory, thus improving the sensing sensitivity.

Figure 8:
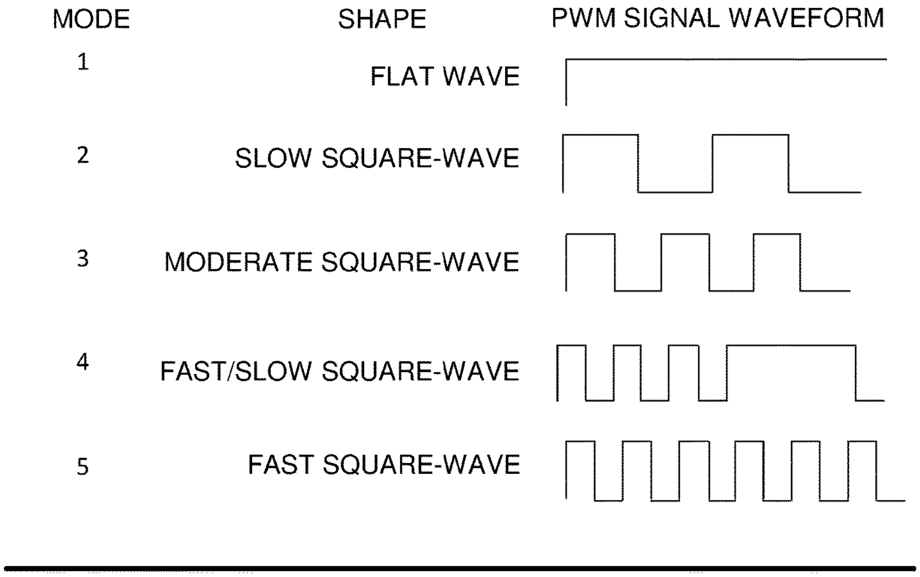
FIG. 8 is a waveform diagram showing control output operation modes of the present invention.

The apparatus 5 preferably also includes a control key 10 arranged on the housing 6, and the control key 10 is connected to the main control unit 9. Preferably, the control key 10 protrudes from the housing 6 so as to facilitate the user in accurate positioning by feel. The main control unit 9 can control the activation of the vibrator 7 or the turn-off of the vibrator 7, or set an output control mode corresponding to the operation to drive the vibrator 7 in response to an operation of the user on the control key 10. For example, for the turn-off state, the vibrator is activated by pressing the control key for a long time; and for the turn-on state, a switch to the vibration mode is realized by pressing the control key for a short time. Preferably at least one output control mode is pre-stored in the main control unit, and the output control mode is used to control the massage apparatus to be in a corresponding operation mode. The output control mode is not influenced by the operation of the sensor. The output control mode corresponds to a vibration mode, and the main control unit outputs a kind of PWM signal continuously so as to keep the massage apparatus in a vibration mode continuously. As shown in FIG. 8, five different kinds of PWM signals are preferably provided, and the main control unit controls the massage apparatus to be in five different vibration modes in response to the operation on the control key, providing experience of several massage modes to the user so as to better meet the user requirements. The control of the vibration speed triggered by the sensor is achieved by changing the duty cycle of the PWM signal, and the vibration speed can be adjusted and controlled in different vibration modes.

Preferably, the vibration massage apparatus 5 further comprises a storage unit connected to the main control unit 9 and configured to store the output control mode and the output of the vibrator by which the main control unit currently drives the vibrator when the main control unit responds to an operation of turning off the vibrator. The vibration massage apparatus can be controlled to be directly in the recorded vibration mode and speed through the memory function of the vibration massage apparatus when the apparatus is started again, which is convenient for use by the user.

Preferably, a battery assembly 16 is arranged inside the housing 6 of the vibration massage apparatus, the battery assembly 16 is connected to the vibrator 7 and the main control unit 9 respectively, and the battery assembly 16 comprises a battery pack 17 and a charging circuit connected to the battery pack 17. The battery assembly 16 is used to power the vibrator 7 and the main control unit 9, and to charge the battery pack 17 by being connected to an external power source to ensure the normal operation of the apparatus. Preferably, the battery assembly further comprises a charging wire 32 matching with the charging circuit and used for connecting the external power source and the charging circuit so as to charge the battery pack. It is also within the skill of the art to provide wireless charging of the battery pack 17.

Further, the outer surface at a second end 37 of the housing 6 opposite the rounding 12 on the main outer surface 11 of the apparatus is formed as an approximate plane 14, that is, substantially a plane, and may have a certain arc shape. Preferably, it is configured to be slightly raised so as to optimize the hand feel. The sensor is arranged close to the approximate plane 14, preferably close to the approximate plane 14 as much as possible. The sensing surface is opposite to the approximate plane and the sensing range is toward the outer surface. Preferably, multiple bumps or pits 36 may be disposed at the positions on the outer surface of the approximate plane 14 corresponding to the sensor so as to form an arc-shaped notification bar, which is convenient for the user in the positioning operation, particularly under dim or dark lighting. Preferably, the bumps or pits may be also arranged to have a function of notifying the change of the speed corresponding to the direction of the trajectory. For example, the vibration speed is decreased accordingly based on the direction from left to right of the trajectory, and the distribution of the bumps or pits 36 is arranged to gradually become being dense from being sparse or gradually become being small from being big from left to right for illustration.

The apparatus 5 preferably further includes a sleeve 15 covering the housing 6 and defining a main outer surface 11. The sleeve 15 has some flexibility and elasticity, and is preferably made of silica gel material. Preferably, the main outer surface 11 of the apparatus is defined by the sleeve in a completely surrounding way. A charging socket 18 with a tethered matching sealing cap 19 is arranged at a position on the sleeve 15, for realizing dustproof and waterproof operation, the charging socket being connected to the charging circuit 30 that is located within the housing 6.

In another variation of the present invention, a vibration dildo comprising the vibration massage apparatus described above is further provided. As shown in FIGS. 2 and 3, the sleeve 15 of the vibration massage apparatus presented as a vibration dildo includes a main portion 31 (corresponding to the insertable portion 13 described above) of a shape of an erect penis and a laterally protruded arm 20. The position and the shape of the arm 20 preferably facilitates the arm 20 in making a contact with the clitoris of the user of the dildo. Another or auxiliary vibrator 7 incorporating a motor 34 of the arm 20 shown in FIG. 3 is located in the arm 20, and the auxiliary vibrator is connected to the main control unit 9 and configured for driving the arm 20 to vibrate.

The sensor 8 is arranged at a position away from the main portion 31 and the arm 20. Preferably, the end surface (the approximate plane 14 shown in FIG. 3) proximate the second end 37 opposite to the insertable portion 13 on the vibration dildo is arranged to be oriented obliquely upward and close to the arm 20. Thus, it can be seen that the vibration dildo tilts up along the extending direction of the vibrating dildo, so that the hand of the user who is being massaged can easily approach the sensor 5, thus facilitating control by gestures of the user.

In an exemplary embodiment as shown in FIG. 3 the vibration dildo also includes a silica gel leather case 21 as well as the battery pack 17 inside the housing 6, an electroplated ring 22 mounted on the housing, a silica gel back cover 23 on the housing, a lower cover 24 of the housing, a plurality of screws 25 for fastening the housing, a motor 26 of the main body (within the insertable portion) of the housing, an upper cover 27 of the housing, a flexible board EVA 28 (forming a part of the sensor 5) attached to the housing, and a flexible board 29 attached to the flexible board EVA. The vibration dildo further includes the charging PCB 30 mounted in the housing 6, the silica gel sealing cap 19 for sealing the charging board socket 18, a PCB board 33 in the housing, the charging wire 32 for connecting external power, a motor 34 of the arm and a motor cover 35 covering the motor 34.

The main control unit (MCU) 9 on the PCB board 33 is connected to the sensing detection circuit of the sensor. The sensing point of the detection circuit has a fixed electrical level. When an external object (such as a finger) touches the sensing sheet (namely the above-mentioned flexible board EVA 28) (the sensing sheet is connected to pins of the MCU), the electrical level of the sensing point changes, the MCU main control unit 9 performs analysis and processing based on the electrical signal level variation and sends a corresponding instruction to the drive circuit. The MCU main control unit 9 outputs a PWM signal to the drive circuit by analyzing an input instruction of the key, so that the motor works in different modes and speeds.

Figure 4:
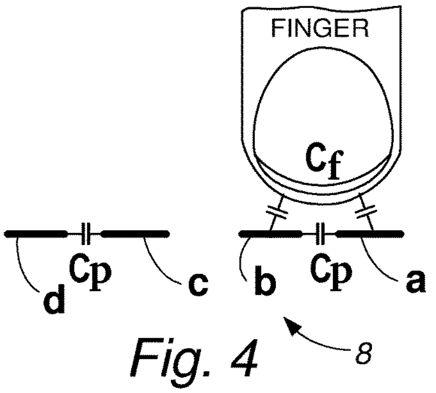
FIG. 4 is a fragmentary sectional view showing a user's finger as an external object in proximate relation to the sensor of FIG. 1.
Figure 5:
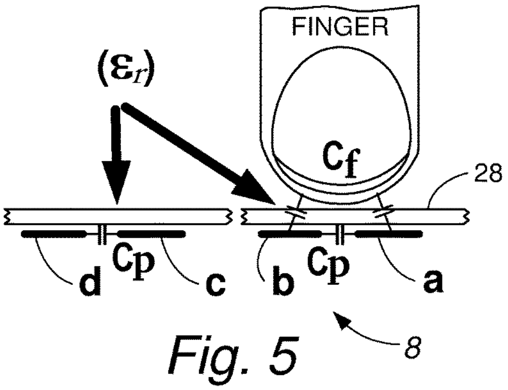
FIG. 5 is a sectional view as in FIG. 4 showing a non-conductive film interposed between the sensor and the user's finger.
Figure 9:
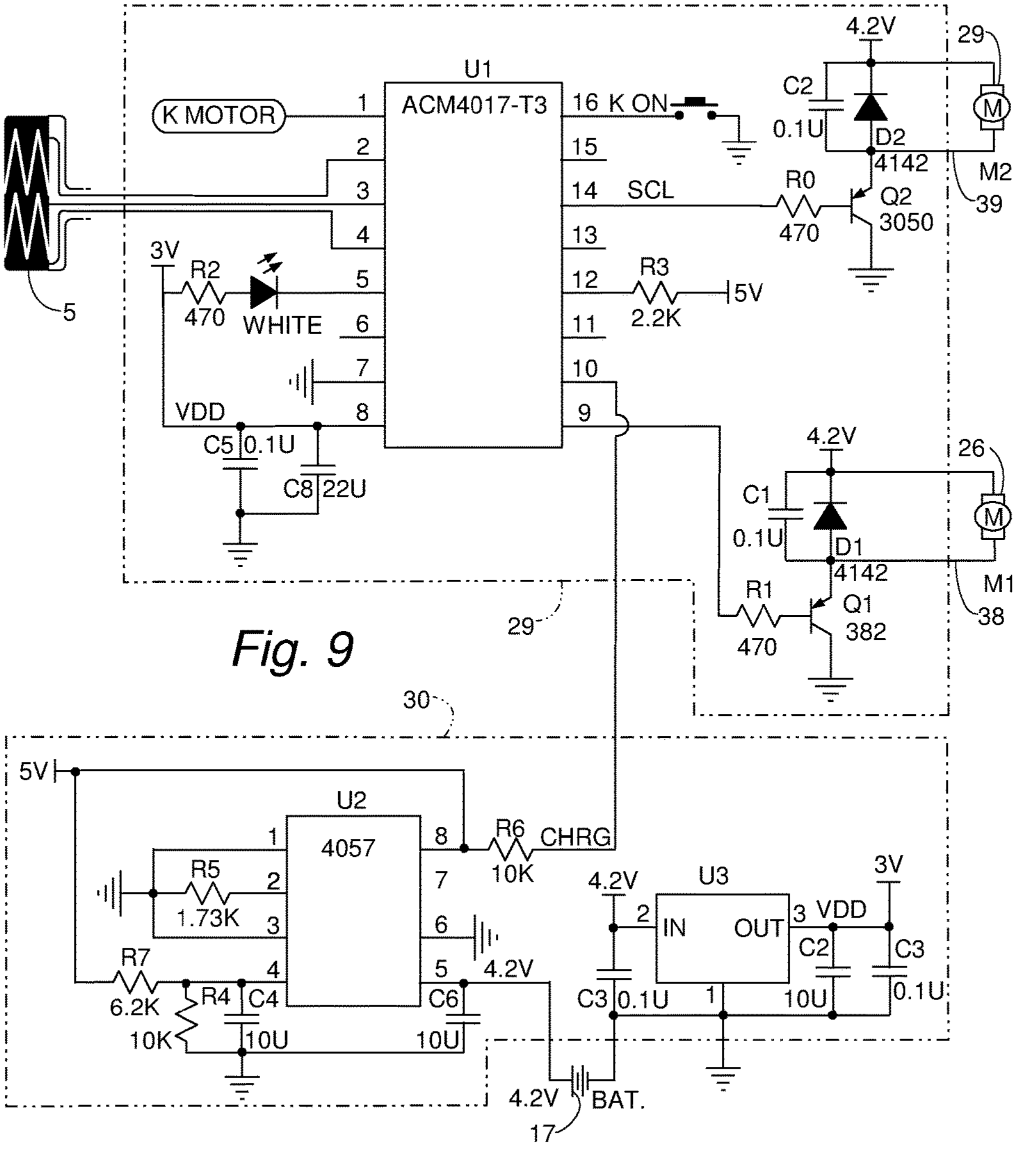
FIG. 9 is a schematic circuit diagram of the massage apparatus of FIG. 2.
Figure 10:
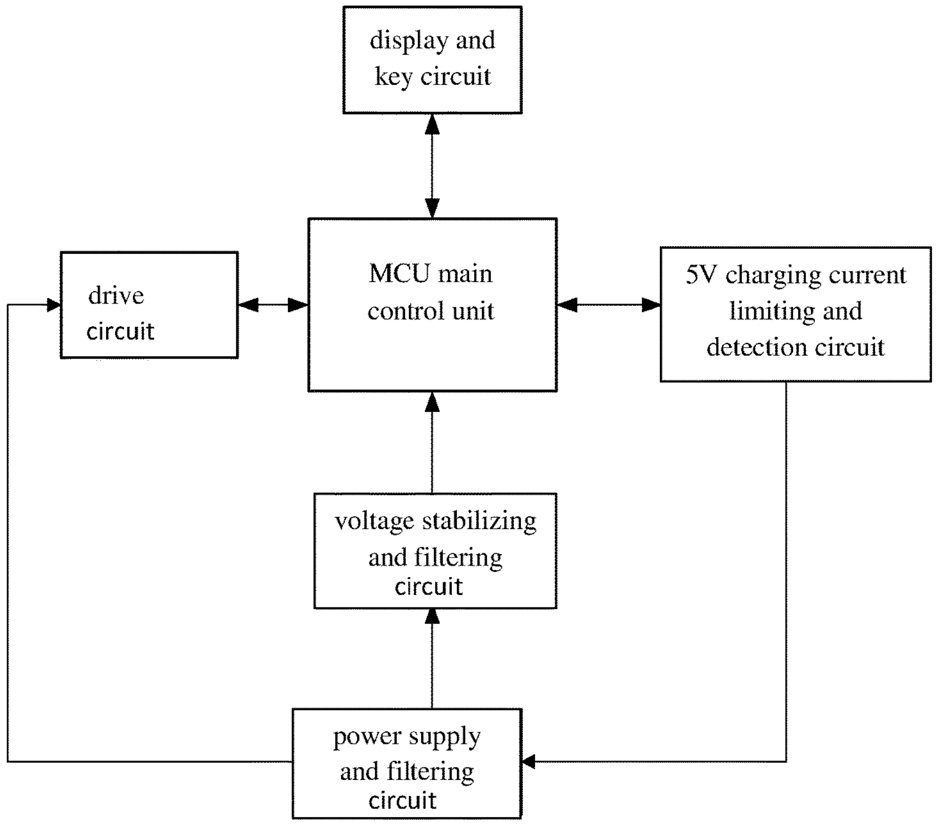
FIG. 10 is a schematic block diagram of the massage apparatus of FIG. 2.

As indicated above, touch sensing technology generally is based on the principle of capacitive sensing, using a relaxation oscillator. There is a parasitic capacitance Cp between adjacent wires or copper foils such as the sensor units a, b, c, etc. of the sensor 8. When a finger touches or gets close to the copper foil, it is equivalent to adding two capacitors, which are equivalent to a capacitor Cf connected in parallel with Cp as indicated in FIG. 4. If there is a non-conductive medium such as the EVA sheet or board 28 between the fingers and the copper foil as depicted in FIG. 5, it will affect Cf. The thicker the medium, the smaller the dielectric constant $\varepsilon r$ of the medium, the greater its impact. A circuit such as that shown in FIG. 6 can be used for detecting Cp and the change of Cp (Cf). The left half of the figure depicts a relaxation oscillator. Detection proceeds as follows: Charge the Cp with an iCHARGE current using a constant current source. When the voltage on Cp rises just above the voltage at the inverting input of the comparator VBG (1.3V), the comparator is flipped to high level, a grounding switch is closed, and Cp rapidly discharges to zero. The comparator flips back to low, and the constant current source charges Cp again, and so on. This process cycle is repeated and produces the oscillation. The period of the oscillation is similar to the charging time: tCHARGE=CpVBG/iCHARGE Specifically, as shown in FIGS. 9 and 10, the circuit structure of the vibration dildo generally comprises: a MCU main control unit, drive circuits (including a first drive circuit and a second drive circuit for driving a motor of the main portion 31 and a motor of the arm 20 respectively), a 5V charging current limiting and detection circuit, a voltage stabilizing and filtering circuit, a display and key circuit (the key including a control key and a sensor) and a power supply and filtering circuit, that are connected to the MCU main control unit respectively. The power supply and filtering circuit is connected to the voltage stabilizing and filtering circuit, the 5V charging current limiting and detection circuit and the drive circuits.

The 5V charging current limiting and detection circuit is used to ensure the normal function of the polymer lithium-ion battery built in the vibration dildo. In case a 5V DC power supply is used to charge the product, the 5V charging current limiting and detection circuit may provide stable voltage and current for the battery, avoiding the damage to the battery. The voltage stabilizing and filtering circuit mainly serves to provide a stable voltage to the MCU main control unit, which is not influenced by the change of the battery voltage. The drive circuit is used to provide a signal to a high-power transistor using a PWM signal. The motor works when the PWM signal is at a high level; the motor stops working when the PWM signal is at a low level; and the motor vibrates rhythmically when the duty cycle of the PWM signal changes rhythmically. The power supply and filtering circuit preferably uses a polymer lithium-ion battery of 3.7V and 700mAH, which is used to power both the MCU and the two drive circuits. The display and key circuit is used to control LED indicators and the mode, and to turn on or turn off the vibrator.

Preferably, there are five modes for the vibration dildo, each mode having three speeds. When the mechanical key (control key) is triggered, the MCU main control unit changes the PWM signal to switch the mode, and meanwhile the LED indicators will also change accordingly. When the sensing sheet is triggered, the MCU changes the duty cycle to adjust the speed.

When the PCB board 33 in the apparatus is activated, the MCU main control unit 9 of the PCB board 33 outputs a PWM signal after receiving a key instruction, so as to drive the drive circuit to control the motor 26 of the main body in the housing and the motor 34 of the arm outside the housing to be started in speed 1 mode (other modes are also possible based on the memory function). The surface of the flexible board 29 is covered with a silica gel back cover 23. When a conductive substance (such as a finger) approaches the silica gel back cover 23, the voltages at three sensing points on the flexible board 29 are changed, and the electrical signal variation is transmitted to the MCU main control unit 9 on the PCB board 33. The MCU main control unit 9 can perform analysis and processing based on the electrical level variation, outputs a corresponding PWM signal and sends a corresponding instruction to the drive circuit. Specifically, as shown in FIG. 1, the sensing sheet adjusts the speed as follows: when the finger is sliding in proximity to or close to the sensing units, if the sensing units a-b, b-c or a-b-c are triggered sequentially, the vibration speed can be increased; otherwise, if the finger is moving away from the sensing units, the vibration speed is decreased. The manufacturer can set a gear for continuous acceleration or deceleration as actually required; for example, a maximum of three consecutive upshift or downshift operations can be supported.

Preferably, the operating mode is suspended during charging, and the LED light flickers; the time period for charging is typically 2 hours. The apparatus can be automatically turned off during use if the battery is out of power, and the battery should be recharged in time. The operation state of motor is indicated by the LED light being synchronously activated with the PWM signal.

Figure 11:
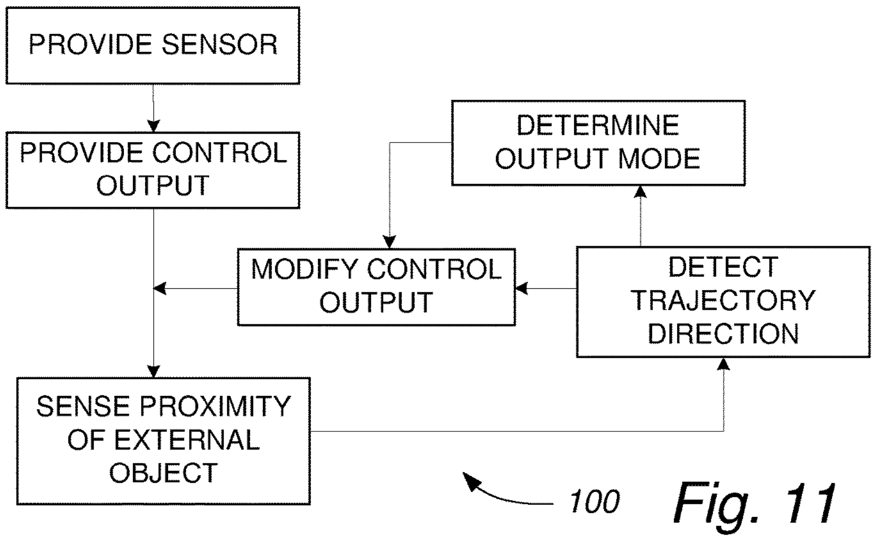
FIG. 11 is a flow chart of a sensing control method according to the present invention.

In a further aspect of the present invention, and with reference to FIG. 11, a sensing control method 100 is provided that is especially effective in controlling the change of an output (such as vibration intensity, heating intensity, rotation frequency, heat generation amount, etc.) of an appropriate device through the sensing of user's gestures.

The sensing control method 100 of the present invention includes providing a sensor used to sense a trajectory of an external object, and controlling the change of the output based on the direction of the trajectory. The sensor can generate different electrical signal variations (which may be pulse variations, electrical signal variations such as current or voltage variations) based on different distances between a sensing point on a sensing detection circuit of the sensor and the external object when the external object approaches the sensor, and the trajectory of the external object and the direction of the trajectory are acquired by analyzing the variation of the sensing point. Furthermore, when the external object is sensed by the sensor in the present embodiment it means that the electrical signal variation of the sensing point on the sensor brought by the external object reaches a preset value, then the sensing point is recorded, and the trajectory is determined by the recorded sensing point. As such, it is ensured that the sensing result is more accurate and mis-triggering of the sensing point is avoided.

In the present embodiment, after the direction of the trajectory of the external object is obtained, the change of the output is controlled according to different control instructions corresponding to different preset directions of the trajectory. For example, if the direction of the trajectory is preset to be from left to right, then the intensity of the output is increased correspondingly; and if the direction of the trajectory is preset to be from right to left, then the intensity of the output is decreased correspondingly.

In the present embodiment, the sensor has at least two sensing units, and the trajectory of the external object can be acquired according to the locations of the sensing units. Since the locations of the sensing units are fixed, if the variation value of the electrical signal of the sensing unit caused by the external object reaches a preset value, then it is determined that the corresponding sensing unit is activated, and a relative distribution of the variation of the electrical signal is generated. Therefore, the direction of the trajectory can be determined according to the sequential order of sensing the external object. For example, the sensing units are designated a and b in order from left to right; if the approaching of the external object is sensed by a and b sequentially, it can be determined that the sensed trajectory direction is from left to right. It should be noted that, if the external object is sensed by the sensing unit designated a and the sensing unit numbered b simultaneously, since there is no trend of direction change, the direction of the trajectory cannot be formed, and the control of the output will not be triggered.

Preferably, the sensor has more than three sensing units. Small actions of external object can be accurately sensed through partitioned sensing, and it is advantageous for determining the direction of the trajectory more efficiently and accurately. For example, a short sensing trajectory is formed on the sensor when a user approaches the sensor. If the number of the sensing units constituting the sensor is appropriate and the gap between the sensing units is appropriate, a short trajectory can be sensed by at least two sensing units, and the direction of the trajectory can be determined efficiently according to the distribution of sensing units.

Preferably, at least two adjacent sensing units are arranged along an expected path P of the trajectory for sensing the direction. That is, only if the single operation of the user is sensed by at least two adjacent sensing units in the sensor, the control of the output will be triggered. Accordingly, the sensor is preferably provided with at least two adjacent sensing units. If the external object is sequentially sensed by two sensing units that are not adjacent to each other, the condition of triggering control is not met. For example, the sensing units are designated a, b and c from left to right, and only a-b, b-c, a-b-c, c-b, b-a, c-b-a can form the direction of the trajectory, wherein a-b means that the approaching of the external object is sensed by the sensing unit numbered a and the sensing unit designated b sequentially. If the external object is sensed by the sensing unit designated a and the sensing unit designated c sequentially, but is not sensed by the sensing unit designated b, the direction of the trajectory will not be formed.

Further, the trajectory sensed by the sensor is preferably valid only if it is sensed within a preset time. Moreover, the trajectory must be sensed by two adjacent sensing units in a preset time interval. Therefore, even if a trajectory is formed by triggering successive sensing units in sequence and the direction of the trajectory can be obtained, if the total length of time for acquiring the trajectory exceeds the preset time, the sensing result is still considered to be invalid. If one of the sensing units is triggered and then other sensing units are triggered after the preset time has been exceeded, the trajectory cannot be formed. For example, the sensing units are designated a, b and c from left to right; if the external object is sensed by the sensing unit designated a, even if the external object is sensed by the sensing unit designated b after the preset time has been exceeded, the direction of the trajectory cannot be formed. Accordingly, as to the operation of the user, if the user approaches the sensing unit designated b, pauses for a few seconds (assuming that the preset time has been exceeded), and then approaches the sensing unit designated c again, such operation will be considered to be invalid and the direction of the trajectory of b-c will not be sensed. Only if the direction of the trajectory is sensed through consistent operations, the control of the output can be triggered effectively, avoiding occurrence of mis-triggering and improving the accuracy of the operation.

Preferably, the control instruction corresponding to the direction of the trajectory is triggered only when the external object can no longer be sensed by the sensor. That is, only if the external object (such as a finger) used by the user for operation leaves the sensing range of the sensor, the detection result of sensing the direction of the trajectory is regarded as a valid input.

In the present embodiment, a single sensing operation of the operator forms only one direction of the trajectory, and accordingly, the output is controlled to change by a preset amount, such as increasing by 5%. If the same direction of the trajectory is sensed continuously, the output is controlled to be increased by a preset amount continuously and incrementally according to the number of times of sensing the direction of the trajectory. For example, if a trajectory in a direction from left to right is sensed firstly, the output is controlled to be increased by 5%. On this basis, if the trajectory in the direction from left to right is sensed again, the output is controlled to be increased by 5% on the basis on the previous output. If the user performs operations in the same direction continuously, the control effect of increasing or decreasing the output incrementally is achieved.

If opposite directions of the trajectory are sensed continuously, the output is changed in an opposite direction to the previous output. That is, if completely opposite directions of the trajectory are sensed successively, the output is controlled to be increased firstly and then decreased, or be decreased firstly and then increased. For example, if the trajectory in the direction from left to right is sensed firstly, then the output is controlled to be increased by 5%. On this basis, if the direction of the trajectory is sensed next time to be from right to left, the output is controlled to be decreased by 5%.

Preferably, in the present embodiment, the method further comprises: presetting at least one output control mode; and setting an output control mode corresponding to a user operation based on user operation control. That is, the output control mode is changed through operation control. The operation control may be triggered by hardware control, such as a key, a button, a knob or the like; or may also be triggered through sensing control. Preferably, a reception subject of the operation is a key or a sensing key additionally provided. The output control mode means that the output is controlled to be output in a mode so that the controlled device is in a corresponding operation mode. The change of the output triggered by the external object will be performed in the output control mode, the mode is not adjusted, and only the output is controlled to be increased or decreased. For example, the controlled device is kept to be in a vibration mode by continuously outputting a kind of PWM signal, and the control triggered by the external object adjusts the output by changing the duty cycle of the PWM signal so as to change the vibration speed of the controlled device.

Preferably, the sensing control method according to the embodiment further provides a memory function, which is configured for recording the current output and the current output control mode in response to a user's operation of turning off the controlled device. When the controlled device is started next time, the controlled device is driven directly according to the recorded output and the recorded output control mode. For example, if the controlled device is currently in mode 2 with speed 3 in response to the turn-off operation, the controlled device will still be in mode 2 with speed 3 when turned on next time.

Preferably, the sensor used in the sensing control method according to the present embodiment is a proximity sensor. The sensing can be triggered as long as the approaching of the external object is sensed, and there is no need to touch the surface of the apparatus. Of course, swiping or touching may bring about better sensing effect.

The sensing control method according to the present embodiment can be well applied to any adjustable device under quantitative or qualitative control, including but not limited to: the adjustment of the mode and brightness of lamps, the adjustment of heating mode and heating temperature of a heater, the adjustment of cooking mode, heating temperature, heating time or the like of a coffee pot, the adjustment of rotational mode and rotational speed of a fan, the up and down adjustment of vehicle window, the volume adjustment and sound effect control of an audio equipment, the adjustment of a blow dryer, a refrigerator or the like, and even the on-off control of a device.

In summary, a sensing control method and apparatus, and a vibration massage apparatus are provided according to the invention. A desirable control effect can be obtained based on the sensed direction of the trajectory of the external object without accurate positioning of the sensor. Not only the convenience of the sensing operation can be improved significantly, but also the control accuracy can be improved; meanwhile, the invention can be well applied to any device for control using several input control signals or variable input control signals for control, thus having a wide range of application and significantly optimizing user experience.

The above described are merely embodiments of the present invention and are not intended to limit the scope of the present invention. All the equivalent transformations made by using the contents of the specification and the drawings of the present invention are directly or indirectly applied to the related technical fields, and are equally comprised within the scope of protection of the present invention.

What is claimed is:

1. A vibration massage control apparatus, comprising:

(a) a housing; a vibrator arranged inside the housing;

(b) a sensor arranged close to the housing;

(c) a main control unit connected to the sensor and having a control output connected to the vibrator, characterized in that the main control unit is configured for acquiring a trajectory direction of a spaced external object sensed by the sensor, the external object being sufficiently close to and not necessarily touching the sensor and for changing the control output to the vibrator, based on the acquired trajectory direction, wherein:

(d) the sensor has at least two sensing units for generating corresponding electrical signal variations;

(e) the trajectory direction is acquired by the main control unit according to a relative distribution of the electrical signal variations;

(f) the trajectory direction is acquired by the main control unit according to a relative distribution of the electrical signal variations;

(g) adjacent ones of the at least two sensing units of the sensor are separated by a gap;

(h) at least a portion of the gap is oriented obliquely relative to the expected trajectory path; and (i) the gap forms a zigzag pattern.

2. The vibration massage apparatus according to claim 1, wherein a vibration speed of the vibrator is increased or decreased by the main control unit based on the acquired trajectory direction.

3. The vibration massage apparatus according to claim 1, comprising at least three sensing units, and the sensing units are distributed adjacently and separated by respective gaps.

4. The vibration massage apparatus according to claim 3, wherein the sensing units are arranged in an arc shape or in a straight line.

5. The vibration massage apparatus according to claim 1, wherein the trajectory direction is acquired during a preset time interval.

6. The vibration massage apparatus according to claim 1, wherein if the trajectory direction is acquired continuously, the control output which drives the vibrator is correspondingly continuously increased or decreased.

7. The vibration massage apparatus according to claim 1, wherein if a continuously sensed trajectory direction reverses to an opposite direction, the main control unit controls the control output to be changed in an opposite direction to a previous change of output.

8. The vibration massage apparatus according to claim 1, wherein the vibration massage apparatus further comprises:

(a) a control key located on the housing, the control key being connected to the main control unit;

(b) at least one output control mode stored in the main control unit; and (c) the main control unit is configured for selectively:

(i) activating or turning off an external device; and (ii) setting an output control mode in response to an operation of the control key.

9. The vibration massage apparatus according to claim 8, further comprising a storage unit, the storage unit being connected to the main control unit, and configured for storing the output control mode and the control output by which the main control unit currently drives the vibrator when the main control unit responds to a further operation of the control key for turning off the vibrator.

10. The vibration massage apparatus according to claim 1, wherein the housing has a main outer surface having opposite first and second end portions, an insertable portion of the housing being formed by a rounding at the first end portion of the main outer surface, and the sensor is located away from the insertable portion.

11. The vibration massage apparatus according to claim 10, wherein the sensor is located close to the second end portion.

12. The vibration massage apparatus according to claim 10, further comprising:

(a) a battery assembly located inside the housing, the battery assembly comprising a battery pack and a charging circuit connected to the battery pack;

(b) the battery assembly being connected for powering the vibrator and the main control unit, and (c) the charging circuit being adapted for receiving power from an external power source.

13. The vibration massage apparatus according to claim 12, further comprising:

(a) a charging socket connected to the charging circuit for receiving external power, the charging socket being located proximate the second end portion of the main outer surface; and (b) a sealing cap for the charging socket, the sealing cap being tethered at a position on the sleeve proximate the charging socket.

14. The vibration massage apparatus according to claim 10, further comprising a sleeve covering at least the insertable portion of the main outer surface.

15. A vibration dildo comprising the vibration massage apparatus according to claim 14, characterized in that the main outer surface is of a shape of an erect penis.

16. The vibration dildo according to claim 15, wherein the sensor is accessible for touching during massage.

17. The vibration dildo according to claim 15, wherein the sleeve further comprises:

(a) a laterally protruding arm; and (b) an auxiliary vibrator located within the arm, the auxiliary vibrator being connected to the main control unit.

18. The vibration dildo according to claim 15, wherein an opposite second end portion of the outer surface is configured having a proximately planar portion that is oriented obliquely upward and close to the arm, and the sensor is located close to the second end portion.

* * * * *